United States Patent [19]

Jacques

[11] 4,364,008

[45] Dec. 14, 1982

[54] FOCUSING PROBE FOR MOISTURE MEASUREMENT DEVICE

[76] Inventor: Steven L. Jacques, 1918 Woolsey St., Berkeley, Calif. 94704

[21] Appl. No.: 193,329

[22] Filed: Oct. 2, 1980

[51] Int. Cl.$^3$ ............................................. G01R 27/04
[52] U.S. Cl. ............................... 324/58.5 R; 128/632; 324/58.5 C
[58] Field of Search ....................... 324/58.5 C, 58.5 R, 324/58.5 B; 128/632

[56] References Cited

U.S. PATENT DOCUMENTS

| | | | |
|---|---|---|---|
| 2,999,982 | 9/1961 | Broussaud | 324/58.5 B |
| 3,441,844 | 4/1969 | Busher et al. | 324/58.5 A |
| 3,490,037 | 1/1970 | Williams | 324/58.5 B |
| 3,693,079 | 9/1972 | Walker | 378/53 |
| 3,811,087 | 5/1974 | Schmelzer | 324/58.5 A |
| 3,815,019 | 6/1974 | Wilkes | 324/58.5 A |
| 4,013,065 | 3/1977 | Copland et al. | 128/632 |
| 4,052,666 | 10/1977 | Auer et al. | 324/58.5 B |

FOREIGN PATENT DOCUMENTS 1354474  3/1970  United Kingdom.

OTHER PUBLICATIONS

"A Nondestructive Method for Measuring the Complex Permittivity of Dielectric Materials at Microwave Frequencies Using an Open Transmission Line Resonator" by E. Tanabe & W. T. Joines, *IEEE Transactions On Instrumentations and Measurement*, vol. 1m-25, No. 3, Sep. 1976.

"Transepidermal Water Loss from Dry and Normal Skin" by J. Leveque, J. Garson and J. de Rigal.

*Primary Examiner*—Stanley T. Krawczewicz
*Attorney, Agent, or Firm*—Limbach, Limbach & Sutton

[57] ABSTRACT

In an apparatus for measuring the moisture content of a target material, the apparatus has means for generating an electromagnetic wave of a microwave frequency. The electromagnetic wave is guided by a guiding means. Detecting means are provided for detecting the wave. Focussing means are provided to focus the wave onto the target, at a specified depth, which is adjustable.

15 Claims, 14 Drawing Figures

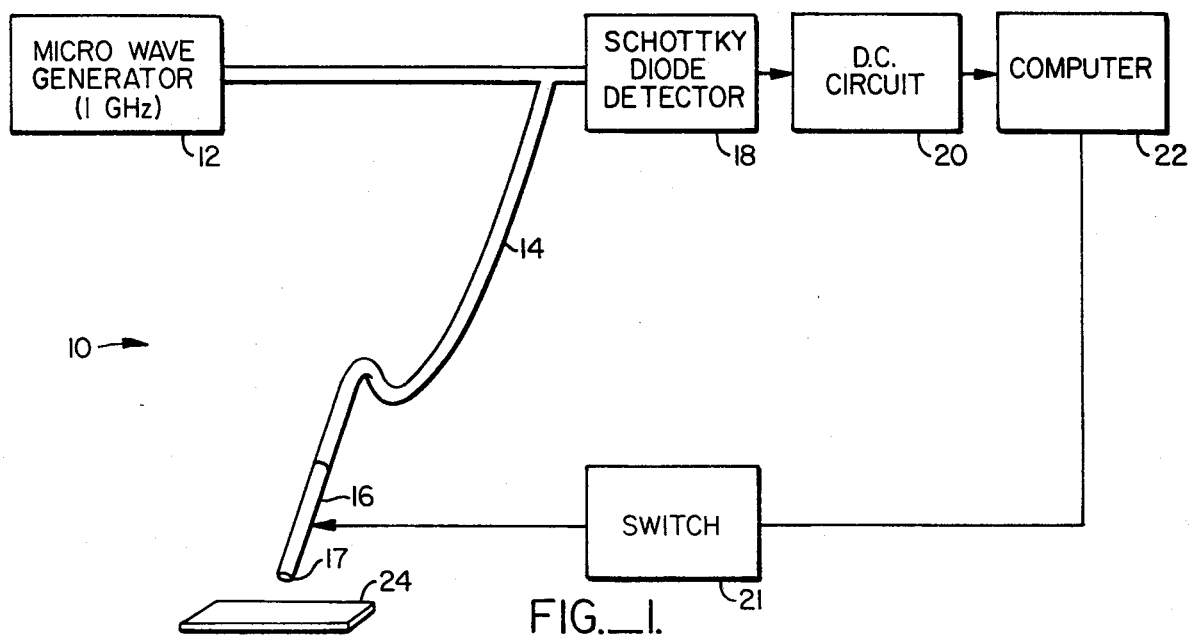
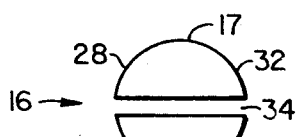
FIG._2a.
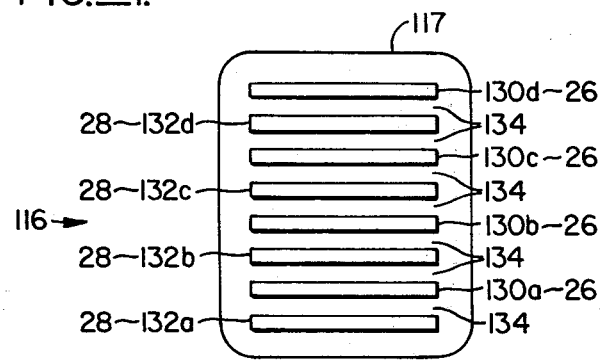
FIG._2b.
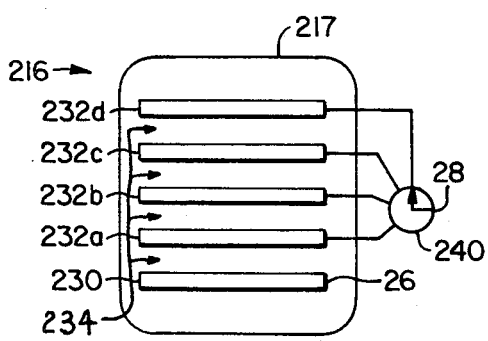
FIG._2c.
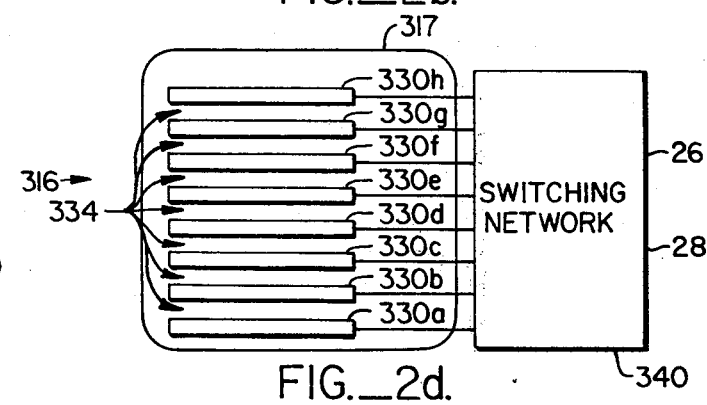
FIG._2d.
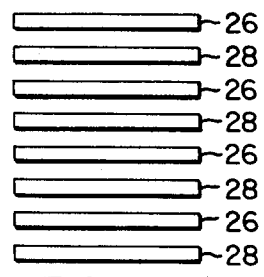
FIG._3a.
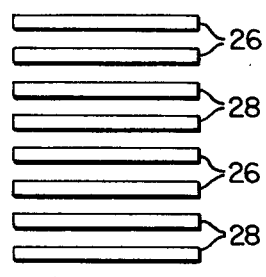
FIG._3b.
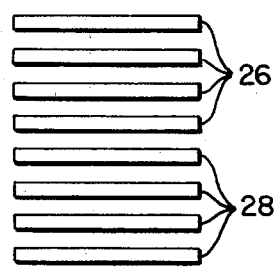
FIG._3c.

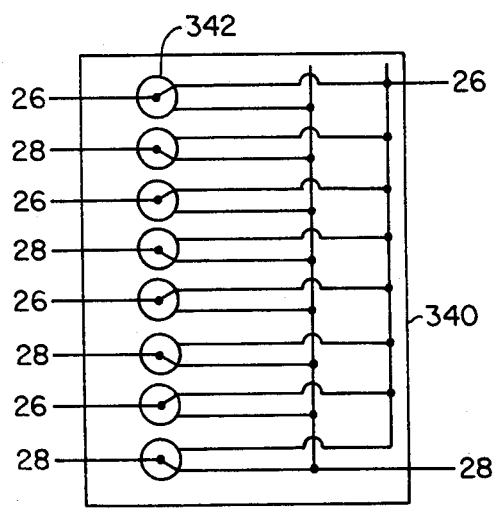
FIG._4.
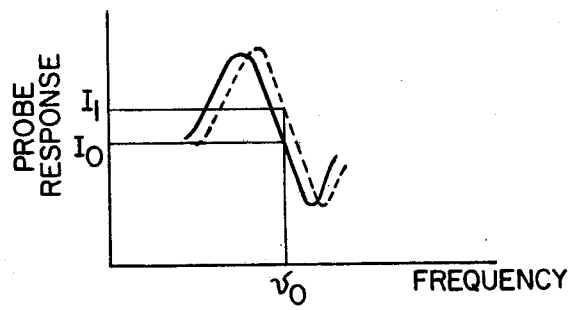
FIG._5.
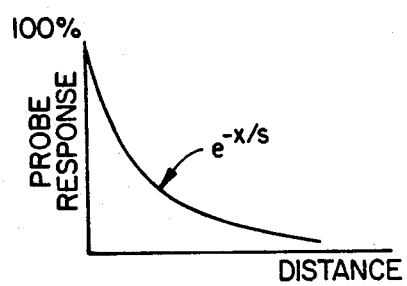
FIG._6a.
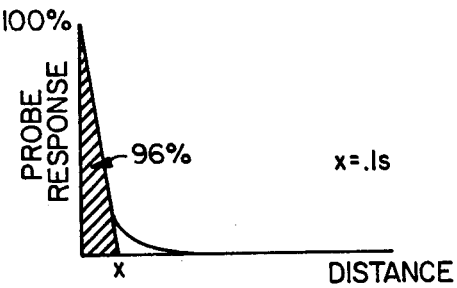
FIG._6b.
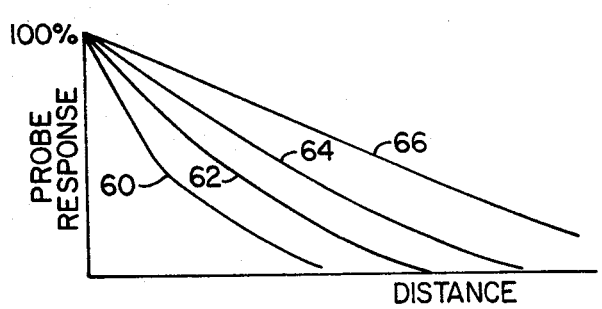
FIG._6c.
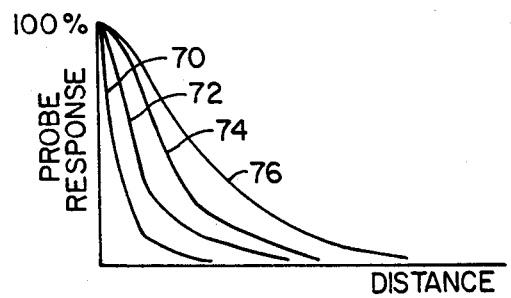
FIG._6d.

FOCUSING PROBE FOR MOISTURE MEASUREMENT DEVICE

BACKGROUND OF THE INVENTION

The present invention relates an apparatus for measuring the moisture content of a target, and more particularly, to a moisture measuring device with a focussing probe.

The use of electromagnetic field of microwave frequency to measure the moisture content of various targets is well known. See, for example, U.S. Pat. Nos. 3,441,844, 3,811,087, 3,815,019, and 4,052,666. See also, Great Britian Pat. No. 1,354,474. In an article entitled "A Non Destructive Method For Measuring The Complex Permittivity Of Dielectric Materials At Microwave Frequencies Using An Open Transmission Line Resonator" which appeared in *IEEE Transactions On Instrumentations And Measurement,* volume 1m-25, No. 3, September 1976, the authors, Eiji Tanabe and William T. Joines described a moisture measuring apparatus using electromagnetic field of microwave frequency and a resonating cavity to guide the microwave onto the target.

U.S. Pat. No. 4,013,065 teaches a moisture measuring apparatus to measure the moisture content of the stratum coreum of human skin by means of a stray field capacitor in an RC network with a 9 KHz oscillator as a source of electromagnetic field. The teaching of that patent, however, is the use of the principle of a "stray field capacitor" to measure the moisture content of the human skin. In the theory of operation, a resistor and a capacitor form a voltage divider for the output of the 9 KHz oscillator, with the junction of the capacitor and resister forming the pickup point for signal processing. The capacitor is placed against the human skin. The stray field of the capacitor penetrates the human skin and is influenced by the moisture content of the skin. The amount of moisture causes an increase in the probe capacitance. The resultant increase in capacitance causes an increase in current in the circuit formed by the series of the resistor and probe capacitor. This increased current causes a greater voltage drop across the resistor and a lower voltage at the junction of the resister and the capacitor. This change in voltage is the transduced signal output used for indicating the amount of moisture. However, the use of a measuring device operating at 9 KHz can result in ambiguous readings. At 9 KHz, many other materials such as: salts, proteins, charged cell membranes, and other solutes may also affect the stray capacitance of the probe capacitor, and thereby after the measurement of the moisture content.

A paper entitled "Linear Measurement of the Water Content of The Stratum Corneum of Human Skin Using a Microwave Probe", by the applicant was published on Oct. 6, 1979 in the IEEE Engineering in Medicine and Biology Society 1st Annual Conference held in Denver, Colo., relating to the present invention.

SUMMARY OF THE INVENTION

In accordance with the apparatus of the present invention for measuring the moisture content of a target, the apparatus comprises means for generating an electromagnetic wave of a microwave frequency, means for guiding the wave, means for detecting the wave, and means for focussing the wave onto the target.

The present invention is also directed to a focussing probe for use with an electrical measuring device to measure a parameter of a target material at various depths. The focussing probe comprises a plurality of spaced conductors, and a switching means for switching the electrical connection between the measuring device and the conductors, such that a plurality of measurements of the parameter are made at various depths.

BRIEF DESCRIPTION OF THE DRAWINGS

FIG. 1 is a schematic overview of the moisture measurement device of the present invention.

FIG. 2(*a–d*) are various enlarged schematic end views of the face of the focussing probe used in the moisture measurement device of the present invention.

FIG. 3(*a–c*) show the different possible electrical connections to the focussing probe of FIG. 2(*d*).

FIG. 4 is one embodiment of the switching network of the focussing probe, shown in FIG. 2(*d*).

FIG. 5 is a graph of probe response versus frequency, showing the principle of operation of the device of the present invention.

FIG. 6(*a–d*) are graphs of probe response versus distance from the probe for the corresponding probes shown in FIG. 2(*a–d*).

DETAILED DESCRIPTION OF THE DRAWINGS

Referring to FIG. 1, there is shown a schematic view of the moisture measuring device 10 of the present invention. The moisture measuring device 10 comprises a microwave generator 12, generating a microwave therefrom. Typically, the microwave frequency is between 100 MHz and 20 GHz. In FIG. 1, the microwave generator 12 operates at a frequency of approximately 1 gigahertz (1 GHz). The microwave generated is transmitted by a guiding means 14, which is a resonant cavity. Such a cavity can typically be a coaxial cable. The guiding means 14 terminates at a probe 16, which will be discussed in detail hereinafter. Along the guiding means 14 is a Shottky diode detector 18, to measure the intensity of the microwave at a select position. The wave detected by the Shottky diode detector 18 is entered into a DC circuit 20. From the DC circuit 20 the signal is entered into a computer 22 which processes the signal sensed by the detector 18 to display the amount of the actual moisture content of the target being measured. A switch 21, under the control of the computer 22, is used to switch the probe 16, as will be discussed hereinafter. The components of the microwave generator 12, the Shottky diode detector 18, the DC circuit 20, the computer 22, and the guiding means for the resonating cavity 14 are all well known and will not be discussed hereinafter. The device 10 of the present invention is adapted to measure the moisture content of a target 24. The target 24 may be, for example, human skin tissue. In the operation of the device 10 of the present invention the target 24 is placed immediately adjacent to the face 17 of the focussing probe 16.

Referring to FIGS. 2(*a–d*) there is shown various embodiments of the focussing probe 16. The coaxial cable, forming the resonant cavity 14, terminates in two connectors, a first connector 26 and a second connector 28. In FIG. 2(*a*), the face 17 of the focussing probe 16 comprises two conductors, a first conductor 30 and a second conductor 32 with a gap 34 therebetween. The first connector 26 of the coaxial cable of the resonant cavity 14 is connected to the first conductor 30 while the second connector 28 of the coaxial cable 14 is connected to the second conductor 32. For the focussing probe 16 shown in FIG. 2(a) to focus the microwave onto the target 24 yet avoiding the radiation of the microwave, like an antenna, the dimension of the face 17 must be less than one-fourth of the wave length of the electromagnetic wave generated by the microwave generator 12. The probe 16 may be formed by any of the well known photo etching techniques whereby initially a layer of conductive material is placed on the face 17 of probe 16. Thereafter requisite gap 34 is etched into the face 17.

Referring to FIG. 2(b) there is shown yet another greatly enlaged end view of a focussing probe 116. At the face 117 of the focussing probe 116, there is a plurality of first conductors 130(a-d). The first conductors 130(a-d) are all connected to the first connector 26 of the coaxial cable 14. Focussing probe 116 also comprises a plurality of second conductors 132(a-d). The plurality of second conductors 132(a-d) are all connected to the second connector 28 of the coaxial cable 14. The plurality of first conductors 130(a-d) and the plurality of second conductors 132(a-d) are positioned in an alternating pattern such that there is a gap 134 between each first conductor 130 and its adjacent second conductor 132. The plurality of gaps 134 formed thereby are of equal dimension. Again, similar to the focussing probe 16 shown in FIG. 2(a) the face 117 of the focussing probe 116 is less than one-fourth of the wave length of the electromagnetic wave generated by the microwave generator 12. Again, similar to the focussing probe 16 of FIG. 2(a), the focussing probe 16 of FIG. 2(b) may be formed by photo etching the interleaf pattern from a layer of conductive material on the face 117 of the probe 116.

Referring to FIG. 2(c) there is shown yet another embodiment of the focussing probe 216. The focussing probe 216 comprises a first conductor 230 and a plurality of second conductors 232(a-d). Each of the second conductors 232(a-d) is positioned at a different distance from the first conductor 230. From FIG. 2(c) it is seen that the distance between first conductor 230 and the second conductor 232(a) is smallest, whereas the distance between first conductor 230 and the second conductor 232(d) is the largest. The first conductor 230 is connected to the first connector 26 of the coaxial cable 14. The plurality of second conductors 232(a-d) are all connected to a switching means 240. Switching means 240 may be a mechanical switch or an electronic switch. One end of the switching means 240 is connected to the second connector 28 of the coaxial cable 14. Thus, by using the switching means 240, various gap dimensions may be presented to the target 24 to measure the various parameters of the target material 24. The switching means 240 may be a part of the switch 21 which is under the control of the computer 22. It should be appreciated that any number of second conductors 232 may be used.

Referring to FIG. 4(d) there is shown still yet another embodiment of the focussing probe 3176. Similar to the focussing probe 216 of FIG. 2(c), which is a multi-depth version of the probe 16 of FIG. 2(a), the focussing probe 316 is a multi-depth version o the focussing probe 16 of FIG. 2(b). The focussing probe 316 comprises a plurality of spaced conductors 330(a-h). Each conductor is spaced at the same constant distance 334 from the conductor immediately adjacent thereto. The conductors 330(a-h) are all connected to the switching network 340. The switching network 340 may be a part of the switch 21 which is under the control of the computer 22. The first and second connector 26 and 28, respectively from the coaxial cable 14 are also connected to the switching network 340. The switching network 340 switches the connection of the first and second connectors 26 and 28 to each of the conductors 330(a-h) such that a plurality of measurements of the moisture content of the target 24 are made at various depths. Again, any number of conductors 330 may be used.

FIGS. 3(a-c) show various possible electrical connection between the conductors 330 and the connectors 26 and 28 of the coaxial cable 14. The relationship between depth measurement and these various possible connections will be discussed hereinafter. FIG. 4 shows one possible embodiment of the switching network 340. A plurality of switches 342 are interposed between each conductor 330 and the connectors 26 and 28.

The theory of operation of the apparatus 10 of the present invention may be understood by referring to FIG. 5. In the absence of any target 24, the microwave generated by the generator 12 is sent along the resonant cavity 14 and terminates at the face 17 of the focussing probe 16. The wave distributes itself such that a standing wave occurs in the resonant cavity 14. When a target 24 is placed against the face 17 of the focussing probe 16, and a parameter, such as moisture, of the target 24 interacts with the microwave, a shift in the frequency of the standing wave occurs. This results in a new standing wave pattern. If a detector 18 were measuring the intensity of the microwave at a fixed position along the guide 14 and at a particular frequency $V_0$, the intensity detected by the detector 18 would shift from $I_0$ to $I_1$ as shown in FIG. 5. The magnitude of the shift from $I_0$ to $I_1$ is determinative of the amount of the moisture in the target material 24 in the depth measured by the focussing probe 16.

The depth to which the microwave of the focussing probe 16 or 216 penetrates into the target 24 is determined by the size of the gap 34 or 234. For the focussing probe 116 or 316 shown in FIGS. 2(b) and 2(d) respectively, the depth to which the microwave penetrates into the target 24 is determined primarily by the spatial frequency of the repeating pattern. In FIGS. 6(a-d) there is shown various graphs of probe response versus distance from the probe, illustrating the penetration of the electric field of the microwave into the target 24 for the various embodiments shown in FIGS. 2(a-d). In FIG. 6(a) it is seen that the intensity of the field generated by the microwave generator 12 decreases exponentially as the distance from the probe increases. In fact, the probe response follows the formula of $e-x/s$ where x is the distance from the probe and s is the spacing of the gap 34 between the conductors 30 and 32.

Referring to FIG. 6(a) there is shown the graph of probe response versus distance for the embodiment of the probe 116 shown in FIG. 2(b). In this example, where the spatial frequency of the repeating pattern is 30 micrometers, at approximately 3 micrometers from the surface of the focussing probe 16, or one-tenth the dimension of the repeating pattern, 96% of the total response is contained within that 3 micrometer distance. The effect of a device, such as that shown in FIG. 2(b) of alternating conductors, is to sharply focus the total response within a very narrow well-defined area.

Referring to FIG. 6(c), there is shown a graph of probe response versus distance for the focussing probe 216 of the embodiment shown in FIG. 2(c). Since there are many possible gap widths, the focussing probe 216 of FIG. 2(c) will have many curves of probe response versus distance. Thus, the focussing probe 216 may be used to measure a parameter content of a target, such as moisture, at various different depths. For example, the curve 60 corresponds to the probe response versus distance for the first conductor 230 and the second conductor 232(a). The amount of moisture measured within that sample volume where $$\text{sample volume} = \text{area of face 17} \times \int_0^\infty [\text{probe response}(x)]dx$$

is taken and is recorded. Next, the switching means 240 switches to the second conductor 232(b) and first conductor 230. That gap is wider than the gap between the first conductor 230 and the second conductor 232(a) and so the depth of penetration is greater. The distance versus intensity response curve is curve 62. The amount of moisture measured would be the amount in the sample volume of curve 62. By subtracting out the amount of moisture that was measured based upon the first conductor 230 and the second conductor 232(a) the sample volume between the regions defined by the first curve 60 and the second curve 62 may thus be calculated. Thus the focussing probe 216 is a multi-depth probe. Similarly, sequential measurements of increasingly deeper sample volumes, and subsequent processing by a computer algorithm can yield a depth profile of the parameter of interest.

Finally, since the focussing probe 316 is a multi-depth version of the focussing probe 116, the curves of probe response versus distance are similar to the response curves shown in FIG. 6(c). In FIG. 6(d), a plurality of curves 70, 72, 74 and 76, show the various curves of probe response versus distance. Curve 70 is similar to curve 60, except it is confined to a narrow region much like the curve of FIG. 6(b) is a narrowly confined version of the curve of FIG. 6(a). Curve 70 corresponds to the connection shown in FIG. 3(a); whereas curve 76 corresponds to the connection shown in FIG. 3(c). Sequential measurements of increasingly deeper sample volumes, and subsequent processing by computer algorithm are again employed, as for focussing probe 216.

It should be appreciated that there are many applications for the apparatus for the present invention. In addition to human skin, tissues and organs, and other organic materials such as the moisture content of leaves, bark, roots, etc. of plant crops in the field may also be measured. In general, the apparatus 10 of the present invention may be used in medicine, agriculture and industry.

There are many advantages to the apparatus 10 of the present invention. First and foremost, the microwave is focussed onto a specified target depth to measure the moisture content of the target. In addition, the multi-depth probe offers advantages in analyzing various parameters, including but not limited to moisture, at various depths of various target materials.

What is claimed is:

1. An apparatus for measuring the moisture content of a target, at a particular depth in said target, wherein said apparatus comprises:
   means for generating an electromagnetic wave of a microwave frequency,
   means for guiding said wave;
   means for detecting said wave; and
   means for focusing said wave onto said depth in said target.

2. In an apparatus for measuring the moisture content of a target, at a particular depth in said target, wherein said apparatus has means for generating an electromagnetic wave of a microwave frequency; means for guiding said wave; and means for detecting said wave; wherein the improvement to said apparatus comprises:
   means for focusing said wave onto said depth in said target.

3. The apparatus of claims 1 or 2 wherein said target is an organic material.

4. The apparatus of claim 3 wherein said organic material is skin tissue.

5. The apparatus of claim 4 wherein said focusing means comprises:
   two conductors with a gap therebetween.

6. The apparatus of claim 4 wherein said focusing means comprises:
   a plurality of first conductors;
   a plurality of second conductors;
   said first conductors are all electrically connected;
   said second conductors are all electrically connected;
   said first and second conductors positioned in alternating pattern with a gap between each first conductor and its adjacent second conductor; and
   each gap is of equal dimension.

7. The apparatus of claim 4 wherein said focusing means comprises:
   a plurality of spaced electrical conductors; and
   means for switching the electrical connection from said guiding means to said conductors such that a plurality of measurements of moisture content are made at various depths of said target.

8. The apparatus of claim 7 wherein:
   said conductors further comprise a first electrical conductor and a plurality of second electrical conductors;
   each of said second conductors is spaced apart from said first conductor, with the distance between each second and first conductors different; and
   said switching means adapted for switching the electrical connection between said guiding means and said second conductors.

9. The apparatus of claim 7 wherein:
   each of said conductors is positioned at an equal distance from the conductor immediately adjacent thereto; and
   all of said conductors are connected to said guiding means through said switching means.

10. The apparatus of claim 5 wherein the planar dimension of said focussing means immediately adjacent to and facing said target is less than one-fourth of the wavelength of the electromagnetic wave.

11. The apparatus of claim 10 wherein said microwave frequency is between 100 MHz and 20 GHz.

12. The apparatus of claim 11 wherein said guiding means is a resonant cavity.

13. A focusing probe for use with an electrical measuring device to measure a parameter of a target material at various sample depths comprising
   a plurality of spaced electrical conductors; and
   means for switching the electrical connection from said measuring device to said conductors such that a plurality of measurements of said parameter are made at various sample depths.

14. The probe of claim 13 wherein:

said conductors further comprise a first electrical conductor and a plurality of second electrical conductors;

each of said second conductors is spaced apart from said first conductor, with the distance between each second and first conductors different; and said switching means adapted for switching the electrical connection between said measuring device and said second conductors.

15. The apparatus of claim 13 wherein:

each of said conductors is positioned at an equal distance from the conductor immediately adjacent thereto; and all of said conductors are connected to said measuring device through said switching means.

* * * * *